US008689981B2

(12) United States Patent
Stone et al.

(10) Patent No.: US 8,689,981 B2
(45) Date of Patent: Apr. 8, 2014

(54) MANIPULATION OF PARTICLES IN CHANNELS

(75) Inventors: Howard A. Stone, Princeton, NJ (US); Mara G. Prentiss, Belmont, MA (US); Pierre Striehl, Cambridge, MA (US); Efraim Feinstein, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 84 days.

(21) Appl. No.: 13/262,079

(22) PCT Filed: Apr. 8, 2010

(86) PCT No.: PCT/US2010/001056
§ 371 (c)(1),
(2), (4) Date: Dec. 13, 2011

(87) PCT Pub. No.: WO2010/117458
PCT Pub. Date: Oct. 14, 2010

(65) Prior Publication Data
US 2012/0080360 A1    Apr. 5, 2012

Related U.S. Application Data

(60) Provisional application No. 61/168,519, filed on Apr. 10, 2009.

(51) Int. Cl.
*B03C 1/00*    (2006.01)
(52) U.S. Cl.
USPC ......... 209/214; 209/215; 209/223.1; 209/232
(58) Field of Classification Search
USPC .............................. 209/214, 215, 223.1, 232
See application file for complete search history.

(56) References Cited

U.S. PATENT DOCUMENTS 3,483,969 A    12/1969  Rosensweig
3,608,718 A *  9/1971  Aubrey et al. ............... 209/214
(Continued)

FOREIGN PATENT DOCUMENTS

EP    1 563 908 A1    8/2005
WO    WO 01/49419 A1    7/2001
(Continued)

OTHER PUBLICATIONS

International Search Report dated Aug. 19, 2010 in International Application No. PCT/US10/001056.
(Continued)

*Primary Examiner* — David H Bollinger
(74) *Attorney, Agent, or Firm* — Wolf, Greenfield & Sacks, P.C.

(57) ABSTRACT

Systems and methods for the manipulation of particles within channels such as microfluidic channels are provided. In one set of embodiments, magnets are positioned around a channel. As a fluid containing magnetic and non-magnetic particles flows through the channel, the magnetic field created by the magnets can be used to transport the magnetic and/or non-magnetic particles to desired locations within the channel, which may useful in some cases for causing some separation of the particles. For example, the magnetic field may be used to transport magnetic or non-magnetic particles from a core fluid to a surrounding sheath fluid. In some cases, the magnetic field is used to transport non-magnetic particles to a small volume within the channel (e.g., a single-file row within the channel). The systems and methods described herein may find application in a variety of fields including, for example, continuous sorting of cells, removal of targeted cells from a stream of blood, or the arrangement of non-magnetic particles in channels for analysis.

22 Claims, 17 Drawing Sheets

(56) References Cited

U.S. PATENT DOCUMENTS

| | | | |
|---|---|---|---|
| 3,951,784 A | | 4/1976 | Kaiser et al. |
| 4,085,037 A | | 4/1978 | Quets et al. |
| 4,521,303 A | | 6/1985 | Hicks et al. |
| 4,920,061 A | | 4/1990 | Poynton et al. |
| 5,076,950 A | | 12/1991 | Ullman et al. |
| 5,186,827 A | | 2/1993 | Liberti et al. |
| 5,358,707 A | | 10/1994 | Reichert et al. |
| 5,466,574 A | * | 11/1995 | Liberti et al. ............... 435/5 |
| 5,762,204 A | | 6/1998 | Yang et al. |
| 5,817,458 A | | 10/1998 | King et al. |
| 5,968,820 A | | 10/1999 | Zborowski et al. |
| 6,231,760 B1 | | 5/2001 | Siddiqi |
| 6,432,630 B1 | | 8/2002 | Blankenstein |
| 6,744,038 B2 | | 6/2004 | Wang et al. |
| 6,822,180 B2 | * | 11/2004 | Fujii et al. ............... 209/128 |
| 6,994,219 B2 | | 2/2006 | Roth et al. |
| 8,292,083 B2 | * | 10/2012 | Varghese et al. ............ 209/39 |
| 2003/0175980 A1 | | 9/2003 | Hayenga et al. |
| 2004/0076525 A1 | | 4/2004 | Olivier et al. |
| 2004/0262210 A1 | | 12/2004 | Westervelt et al. |
| 2005/0137334 A1 | | 6/2005 | Mondain-Monval et al. |
| 2005/0207940 A1 | | 9/2005 | Butler et al. |

FOREIGN PATENT DOCUMENTS

| | | |
|---|---|---|
| WO | WO 2004/002627 A2 | 1/2004 |
| WO | WO 2004/091763 A2 | 10/2004 |
| WO | WO 2005/021151 A1 | 3/2005 |
| WO | WO 2005/072855 A1 | 8/2005 |
| WO | WO 2006/096571 A2 | 9/2006 |

OTHER PUBLICATIONS

Feinstein, E., et al., "Three-dimensional self-assembly of structures using the pressure due to a ferrofluid in a magnetic field gradient," *Journal of Applied Physics*, vol. 99, pp. 064901-1-064901-6, (date not provided) (2006).
Hairer, G., et al., "Experiments on hydrodynamic focusing of non coaxial sheath flows," *IEEE Sensors*, pp. 431-434 (Oct. 22-25, 2006).
Winkleman, A., et al., "A magnetic trap for living cells suspended in a paramagnetic buffer," *Applied Physics Letters*, vol. 85, No. 12, pp. 2411-2413 (Sep. 20, 2004).
Yang, R., et al., "Microfabrication and test of a three-dimensional polymer hydo-focusing unit for flow cytometry applications," *Sensors and Actuators*, vol. 118, pp. 259-267 (date not provided) (2005).
Invitation to Pay Additional Fees mailed Feb. 7, 2010 in International Application No. PCT/US2010/001056.
International Preliminary Report on Patentability mailed Oct. 20, 2011 in International Application No. PCT/US2010/001056.
Angell et al., Silicon micromechanical devices. Scientific American Journal. 1983;248:44-55.
Blom et al., On-Chip Hydrodynamic Chromatography Separation and Detection of Nanoparticles and Biomolecules. Anal. Chem., Dec. 15, 2003, 75 (24), pp. 6761-6768.
Carpino et al., Quadrupole magnetic field flow fractionation for the analysis of magnetic nanoparticles. Journal of Physics: Conference Series. 2005;17:174-80.
Chalmers et al., An integrated approach to optimizing immunomagnetic cell separation by quadrupole magnetic flow sorter. Ohio State University and Cleveland Clinic Foundation. 19 pages. Accessed Aug. 12, 2008.
Davis et al., Deterministic hydrodynamics: Taking blood apart. PNAS, Oct. 3, 2006, vol. 103, No. 40, 14779-14784.
Duffy et al., Rapid Prototyping of Microfluidic Systems in Poly(dimethylsiloxane). Anal Chem. Dec. 1, 1998;70(23):4974-84.
Feinstein et al., Three-dimensional self-assembly of structures using the pressure due to a ferrofluid in a magnetic field gradient. J. Appl. Phys. 99, 064901 (2006).
Giddings et al., 'Eddy' Diffusion in Chromatography. Nature 184, 357-358 (Aug. 1, 1959).
Hairer et al., Experiments on hydrodynamic focusing of non coaxial sheath flows. IEEE Sensors 2006, EXCO, Daegu, Korea / Oct. 22-25, 2006, pp. 431-434.
Halverson et al., Manipulation of non-magnetic materials in ferrofluid containing media. MRS Proceedings. MRS Spring Meeting. 2005;877:S9.5.1-.6.
Huang et al., Continuous particle separation through deterministic lateral displacement. Science 304. 987-990 (2004).
Huh et al., Gravity-Driven Microfluidic Particle Sorting Device with Hydrodynamic Separation Amplification, Anal. Chem., Feb. 15, 2007, 79 (4), pp. 1369-1376.
Inokuchi et al., Micro magnetic separator for stem cell sorting system. Proceedings for the $22^{nd}$ Sensor Symposium. Tokyo. Oct. 20-21, 2005:125-8.
Jiang et al., "An integrated microfluidic cell for detection, manipulation, and sorting of single micron-sized magnetic beads" Journal of Applied Physics (vol. 99, Issue: 8) (2006).
Kose et al., A highly effective cellular manipulation and sorting platform. Proceedings for the COMSOL Conference 2007. Boston. 4 pages.
Marziali, et al. An arrayable flow-through microcentrifuge for high-throughput instrumentation. Proc. Natl. Acad. Sci., vol. 96, pp. 61-66, Jan. 1999.
Pamme et al., "Continuous sorting of magnetic cells via on-chip free-flow magnetophoresis," Lab Chip, 2006,6, 974-980.
Pamme et al., "On-Chip Free-Flow Magnetophoresis: Continuous Flow Separation of Magnetic Particles and Agglomerates," Anal. Chem., 2004, 76 (24), pp. 7250-7256.
Thiel et al., "Immunomagnetic cell sorting—pushing the limits" Immunotechnology, vol. 4, Issue 2, Oct. 1998, pp. 89-96.
Winkleman et al., A magnetic trap for living cells suspended in a paramagnetic buffer. Appl. Phys. Lett. 85(12), 2411-3 (Sep. 20, 2004).
Yang et al., Microfabrication and test of a three-dimensional polymer hydro-focusing unit for flow cytometry applications. Sensors and Actuators A 118 (2005) 259-267.
Yellen et al., Arraying Nonmagnetic Colloids by Magnetic Nanoparticle Assemblers. IEEE Transactions on Magnetics. Oct. 2006;42(10):3548-53.
Yellen et al., Programmable self-aligning ferrofluid masks for lithographic applications. IEEE Transactions on Magnetics. Jul. 2004;40(4):2994-6.

* cited by examiner

Magnet dimensions: 25mm x 6.25mm x 3.125mm

Magnet separation: 1mm

MANIPULATION OF PARTICLES IN CHANNELS

RELATED APPLICATIONS

This application is a National Stage Filing under 35U.S.C. § 371 of PCT/US2010/001056, filed Apr. 8, 2010, entitled "Manipulation of Particles in Channels," by Stone, et al., which claims the benefit of U.S. Provisional Patent Application Ser. No. 61/168,519, filed Apr. 10, 2009, entitled "Manipulation of Particles in Channels," by Stone, et al., each incorporated herein by reference.

FIELD OF INVENTION

The present invention relates generally to the manipulation of particles within channels such as microfluidic channels. In some cases, the particles may be manipulated using magnetic fields.

BACKGROUND

There is a large demand for inexpensive devices that allow for convenient and fast manipulation of particles such as non-magnetic particles. Such technologies may be useful, for example, in the separation of non-magnetic particles from magnetic particles. Examples of non-magnetic particles that may be desirable to isolate include beads, cells, and/or biological species, among others. As a specific example, one may desire to separate circulating tumor cells from a bloodstream of a patient. As another example, one may desire to isolate a non-magnetic precipitant of a chemical reaction from a background magnetic fluid. While various schemes have been developed to manipulate and isolate non-magnetic particles such as cells, their speed, efficiency, and affordability have been limited.

SUMMARY OF THE INVENTION

Systems and methods for the manipulation of particles within channels such as microfluidic channels are provided. The subject matter of the present invention involves, in some cases, interrelated products, alternative solutions to a particular problem, and/or a plurality of different uses of one or more systems and/or articles.

In some embodiments, a method is described. The method comprises, in one set of embodiments, applying a magnetic field to a channel containing a core fluid and a cladding fluid surrounding the core fluid. In some cases, the cladding fluid is different from the core fluid and contacting the core fluid at an interface. At least one of the core and cladding fluids may contain magnetic particles in some embodiments. In some instances, at least some of the magnetic particles may cross the interface due to the applied magnetic field.

In another set of embodiments, the method includes applying a magnetic field to a fluid contained within a channel. The channel may have a cross-sectional dimension, and the fluid may comprise magnetic and/or non-magnetic particles. The method can further comprise passing the fluid through the channel such that, after passing through the magnetic field, at least about 90% of the non-magnetic particles are transported to a region comprising no more than about 10% of the cross-sectional dimension of the channel.

In some embodiments, the method comprises providing a channel having a cross-sectional dimension, where the channel contains a fluid comprising magnetic particles and non-magnetic particles, at least in certain instances. The method may further include applying a first magnetic field to a first portion of the fluid contained within the channel, and in some cases, the first magnetic field may comprise a magnetic field minimum positioned within the channel. The method may further comprise applying a second magnetic field to a second portion of the fluid contained within the channel, where the second portion of the fluid being different from the first portion of the fluid. The second magnetic field may comprise a magnetic field minimum positioned within the channel. In one embodiment, the first magnetic field and the second magnetic field are positioned such that an imaginary plane containing a center axis of the channel can be drawn such that the first magnetic field minimum is on a first side of the imaginary plane and the second magnetic field minimum is on an opposite side of the imaginary plane. The method may further comprise causing transport of the non-magnetic particles from a first radial position within the fluid to a second radial position.

In some embodiments, the method may include providing a channel having a cross-sectional dimension and a center axis. In some cases, the channel contains a fluid comprising magnetic particles and non-magnetic particles. The method may further comprise applying a first magnetic field to a first portion of a fluid contained within the channel. In some embodiments, the first magnetic field comprises a first magnetic field minimum positioned at a first distance from the center axis of the channel. The method may further comprise applying a second magnetic field to a second portion of the fluid contained within the channel, where the second portion of the fluid is different from the first portion of the fluid. The second magnetic field may include a second magnetic field minimum positioned at a second distance from the center axis of the channel, where the second distance is substantially different than the first distance. The method may further comprise causing transport of the non-magnetic particles from a first radial position within the fluid to a second radial position.

In still another set of embodiments, the method includes passing a fluid through a channel, the channel defining a center axis therein, the fluid comprising magnetic and non-magnetic particles, while applying a magnetic field to the fluid such that a first portion of the fluid containing the center axis is enriched in non-magnetic particles and a second portion of the fluid is enriched in magnetic particles. The method may further comprise separating the first portion of the fluid from the second portion of the fluid.

In some embodiments, a device is provided. The device may comprise, in some cases, a microfluidic channel surrounded by no more than four magnetic poles. In some cases, the four magnetic poles may define a plane that is substantially perpendicular to an axis of the microfluidic channel defined by a direction of fluid flow within the microfluidic channel. In some embodiments, the four magnetic poles are arranged around the microfluidic channel such that two imaginary axes, being at 90 degrees relative to each other and defining four quadrants between the axes with the intersection of the axes being at the center of the microfluidic channel and the axes being contained within the plane defined by the four magnetic poles, can be positioned such that two or more of the magnetic poles are contained within the same quadrant.

The device may comprise, in some cases, a microfluidic channel surrounded by at least four magnetic poles. In one embodiment, the at least four magnetic poles define a plane that is substantially perpendicular to an axis of the microfluidic channel defined by a direction of fluid flow within the microfluidic channel. In some embodiments, the at least four magnetic poles are positioned such that the distances between each magnetic pole and its nearest neighbor on either side are not substantially the same.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Systems and methods for the manipulation of particles within channels such as microfluidic channels are provided. In one set of embodiments, magnets are positioned around a channel. As a fluid containing magnetic and non-magnetic particles flows through the channel, the magnetic field created by the magnets can be used to transport the magnetic and/or non-magnetic particles to desired locations within the channel, which may useful in some cases for causing some separation of the particles. For example, the magnetic field may be used to transport magnetic or non-magnetic particles from a core fluid to a surrounding cladding fluid. In some cases, the magnetic field is used to transport non-magnetic particles to a small volume within the channel (e.g., a single-file row within the channel). The systems and methods described herein may find application in a variety of fields including, for example, continuous sorting of cells, removal of targeted cells from a stream of blood, or the arrangement of non-magnetic particles in channels for analysis.

In one aspect, one or more magnets may be positioned around a channel, such as a microfluidic channel, to cause at least partial separation of magnetic and/or non-magnetic particles contained within a fluid flowing through the channel. Thus, in various embodiments of the present invention, magnetic and non-magnetic particles may be flowed through a channel and caused to separate using one or more magnets positioned around the channel. For instance, as discussed below, a channel may contain a core fluid and a cladding fluid surrounding the core fluid according to one set of embodiments, and particles may be transported from the core fluid to the cladding fluid or vice versa due to the effects of the magnetic field produced by the magnets. As an example, the core fluid may contain magnetic and non-magnetic particles, and a magnetic field may be applied to enrich the cladding fluid in magnetic particles, relative to the non-magnetic particles. However, as discussed below, the invention is not necessarily limited to core/cladding fluids within a channel, but is more broadly applicable to any one or more fluids that are contained within a suitable channel. For example, particles suspended in a fluid (e.g., non-magnetic particles suspended in a magnetic fluid) can be transferred from one laminar layer to another laminar layer through interaction with the magnetic field.

Figure 1A:
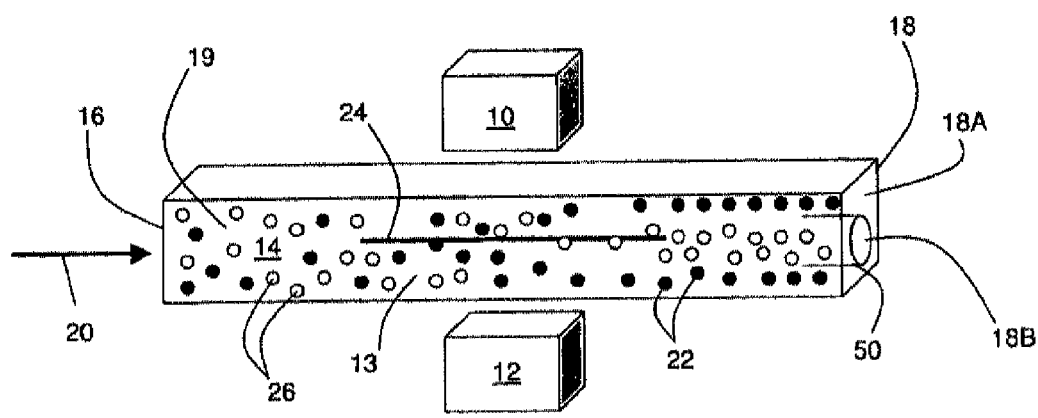
FIGS. 1A-1B include schematic diagrams of fluidic devices according to one set of embodiments.
Figure 1B:
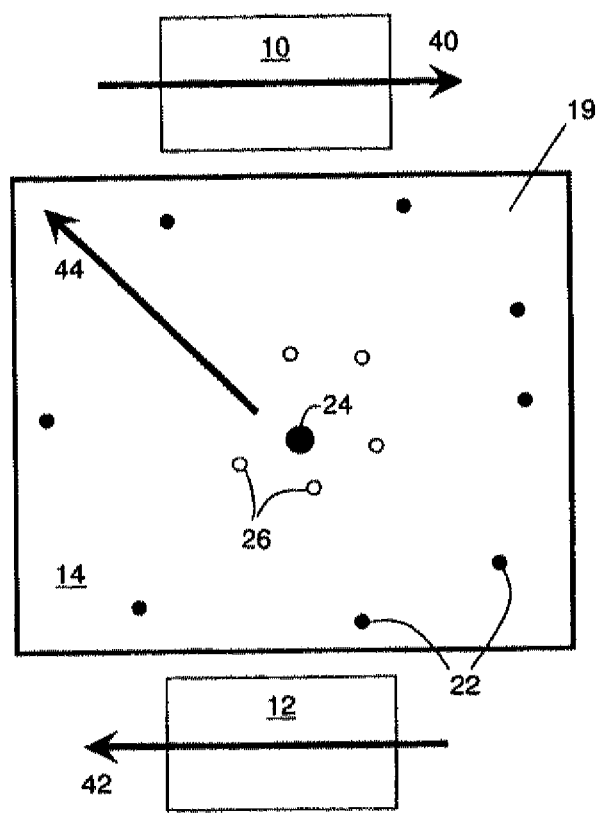

As an example, a system for manipulating magnetic and non-magnetic particles is now provided with reference to FIGS. 1A-1B. In FIG. 1A, fluid 19 passes from left through right through channel 14 in the direction of arrow 20, between inlet 16 and outlet 18. Of course, in some embodiments, channel 14 may be fluidically connected to other channels, for example, within a microfluidic channel network, although these channels are not depicted here, for reasons of clarity. In FIG. 1A, fluid 19 contains magnetic 22 and non-magnetic particles 26 (in other embodiments, however, there may be more than 2 types of particles present, including particles having different degrees of magnetic susceptibility). Magnets 10 and 12 are arranged to produce a magnetic field within region 13 of channel 14. The magnets may include any suitable type of object capable of generating a magnetic field including, for example, permanent magnets, electromagnets, etc. Specific examples of materials that may be used in magnets include, but are not limited to, iron, nickel, cobalt, neodymium (e.g., NdFeB magnets) and some rare earth metals. In some embodiments, the fluid comprising magnetic and non-magnetic particles is passed substantially through the magnetic field (e.g., produced by magnets 10 and 12). A fluid is passed "substantially through" a magnetic field when it is passed through a region with a magnetic field gradient of at least about 0.01 T/mm.

In some embodiments, the magnets may be positioned to create a magnetic field that includes a magnetic field minimum, indicated in this example by region 24 in FIG. 1A. The magnets may be positioned, in certain instances, to create a magnetic field between the magnets that includes a region having a zero magnetic field intensity between the magnets. Additional examples of the positioning of such magnets are also discussed below. In certain embodiments, there may be a magnetic field minimum located within the channel volume. A "magnetic field minimum," as used herein, is given its normal meaning in the art, and refers to a point or line around which the magnitude of the magnetic field does not decrease further in any direction. A magnetic field minimum may refer to a local minimum or an absolute minimum in the magnetic field, and may, in some cases, be defined by a point, line, or curve where the intensity of the magnetic field is zero (i.e., a "magnetic field zero"). However, in other cases, the magnetic field intensity at the magnetic field minimum may not necessarily be zero.

In some cases the magnetic field may be substantially constant along a direction parallel to the flow of fluid within the channel. For example, the magnetic field illustrated in FIG. 1A may be constant along the direction of arrow 20. The use of magnetic fields with little or no variation in the direction of fluid flow may be useful in certain cases, for example, to increase the efficiency of separation of particles, as magnetic field gradients in the direction of fluid flow may cause unwanted mixing, improper separation of the particles, or unwanted trapping effects of particles (e.g., particles suspended in magnetic fluids) in some cases. In some embodiments, the magnetic field gradients may have a non-zero second derivative.

A cross-sectional schematic diagram of the channel shown in FIG. 1A is illustrated in FIG. 1B. As shown in FIG. 1B, the two magnets are positioned on opposite sides of the channel. The first magnet is polarized along a first vector 40, while the second magnet is polarized along a second vector 42 that is parallel to but pointing in the direction opposite first vector 40. Positioning the magnets in this way creates a magnetic field minimum 24 in the form of a line along the center axis (which overlaps with magnetic field minimum 24 in FIG. 1B), going through the plane of the paper (i.e., perpendicularly) in FIG. 1B). In FIG. 1B, the magnitude of the magnetic field increases in a radial direction 44 oriented outwardly away from magnetic field minimum 24 (as well as the center axis). A magnetic field oriented in this manner produces a net force on magnetic particles in the outward radial direction.

In some cases, due to this net force on the magnetic particles, non-magnetic particles may be forced towards the center axis, in the opposite direction of arrow 44, as the magnetic particles cause the non-magnetic particles to become "excluded," thereby causing a net movement of the non-magnetic particles towards the center axis. Such effects may be more strongly seen, in some cases, when the fluid contains a relatively high concentration of particles. That is, higher concentrations of magnetic particles in the fluid may result in a more pronounced movement of non-magnetic particles. Thus, in some embodiments of the invention, the magnetic field in FIGS. 1A-1B may be used to separate the non-magnetic particles from the magnetic particles. As an example, as fluid 19 passes through magnetic region 13, some of magnetic particles 22 within fluid 19 are transported away from the magnetic field minimum 24 (e.g., toward the walls of channel 14). In addition, in this example, non-magnetic particles 26 in the fluid are caused to move towards the magnetic field minimum.

Thus, in some embodiments, such as the examples shown in FIGS. 1A-1B and 3A-3B, the magnets can be arranged to produce a magnetic field having a magnetic field minimum positioned substantially along the center axis of the channel, and in some embodiments, passing a fluid comprising a mixture of magnetic and non-magnetic particles through the channel while applying the magnetic field may produce a first portion, containing the center axis of the channel, that is enriched in non-magnetic particles, and a second portion of the fluid that is enriched in magnetic particles. As used herein, a "center axis" of an object (such as a channel) corresponds to a line intersecting the geometric centers of cross-sectional sections of the object. The center axis of a channel may be, in some embodiments, defined in the direction of fluid flow within the channel.

A "channel," as used herein, means a feature on or in an article (substrate) that at least partially directs flow of a fluid. The channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and/or outlet(s). A channel may also have an aspect ratio (length to average cross sectional dimension) of at least 2:1, more typically at least 3:1, 5:1, 10:1, 15:1, 20:1, or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

"Microfluidic," as used herein, refers to a device, apparatus or system including at least one fluid channel having a largest cross-sectional dimension of less than 1 mm, and a ratio of length to largest cross-sectional dimension of at least 3:1, e.g., perpendicular to fluid flow within the channel. A "microfluidic channel" as used herein, is a channel meeting these criteria. Though in some embodiments, devices of the invention may be microfluidic, in certain embodiments, the invention is not limited to microfluidic systems and may relate to other types of fluidic systems. Furthermore, it should be understood that all or a majority of the channels described herein may be microfluidic in certain embodiments.

The channel may be of any size, for example, having a largest dimension perpendicular to fluid flow of less than about 5 mm or 2 mm, or less than about 1 mm, or less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, positioned to intersect with each other, etc.

The magnetic and non-magnetic particles described herein may include any suitable type of particle. Examples of magnetic particles suitable for use herein include, but are not limited to, magnetically tagged cells, magnetically tagged beads, magnetic droplets, particles (including microparticles and/or nanoparticles) that may be used to form a ferrofluid (e.g., iron particles, iron oxide particles), or particles that may be used to form another type of magnetic fluid (e.g., a solution of paramagnetic ions such as gadolinium ions), among others. Non-magnetic particles that may be used herein include, for example, cells, proteins, viruses, spores, macromolecules, beads (e.g., polymer beads, glass beads, etc.), etc. For example, in some embodiments, the non-magnetic particles comprise porous beads with a relatively large surface area capable of providing a large number of binding sites (e.g., for immuno-reactions such as antibody-antigen reactions). In some instances, the systems and methods described herein may be arranged to separate one type of cell from a population of cells. For example, relatively rare cells (e.g., circulating tumor cells, circulating endothelial cells, mesenchymal stem cells, etc.) may be separated from a larger population of cells, for example, using magnetic tagging techniques, or other methods.

Those of ordinary skill in the art will be familiar with various magnetic particles, and methods for making such particles. For example, pre-polymers may be injected with magnetite and then solidified, to form magnetic hardened polymer beads. Alternatively, magnetite may be deposited onto the surface of a polymer bead to render it magnetic. In some embodiments, magnetic particles or magnetic colloids may be incorporated into drugs, carbohydrates, nucleic acids, proteins, or other biological molecules, which may be incorporated into cells, forming magnetic particles. As a specific example, a magnetic antibody may be selectively attached to a specific cell type (e.g., red blood cells) to form magnetic particles. In some embodiments, red blood cells may exhibit sufficient paramagnetism (e.g., due to the presence of deoxyhemoglobin) to act as a magnetic particle. In some embodiments, particles may be tagged with magnetic entities such as, for example, magnetic nanoparticles (e.g., 10 nm, 50 nm, or 100 nm $Fe_2O_3$ nanoparticles) or magnetic beads (e.g., 1 micron, 4.5 micron, etc. beads) to form magnetic particles. The particles, in some cases, may include microparticles and/or nanoparticles.

The systems and methods employed herein may make use of any suitable fluid, for example, water, saline, blood, oil, buffer solutions, or the like. As used herein, the term "fluid" generally refers to a substance that tends to flow and to conform to the outline of its container. Typically, fluids are materials that are unable to withstand a static shear stress, and when a shear stress is applied, the fluid experiences a continuing and permanent distortion. The fluid may have any suitable viscosity that permits at least some flow of the fluid. In some embodiments, such as those involving the use of core and cladding fluids, immiscible fluids may be used. As used herein, two fluids are "immiscible" when they do not substantially mix over a time scale of the invention, e.g., while the fluids are contained within a channel and are exposed to a magnetic field. Non-limiting examples of fluids include liquids and gases, but may also include free-flowing solid particles (e.g., cells, vesicles, etc.), viscoelastic fluids, and the like.

In some embodiments, more than one fluid is transported through the channel, and the fluids may be distributed in any arrangement within the channel. For example, one or more of the fluids may flow through the channel in a laminar profile, and there may be relatively little mixing of these fluids within the channel. In one set of embodiments, as previously discussed, the fluids may be arranged within the channel in a core-cladding arrangement. Typically, the cladding fluid surrounds the core fluid and prevents the core fluid from contacting the walls of the channel. In some cases, after at least some particle separation has occurred, the core and cladding fluids may be separated and used for different purposes and/or discarded, depending on the application.

Figure 3A:
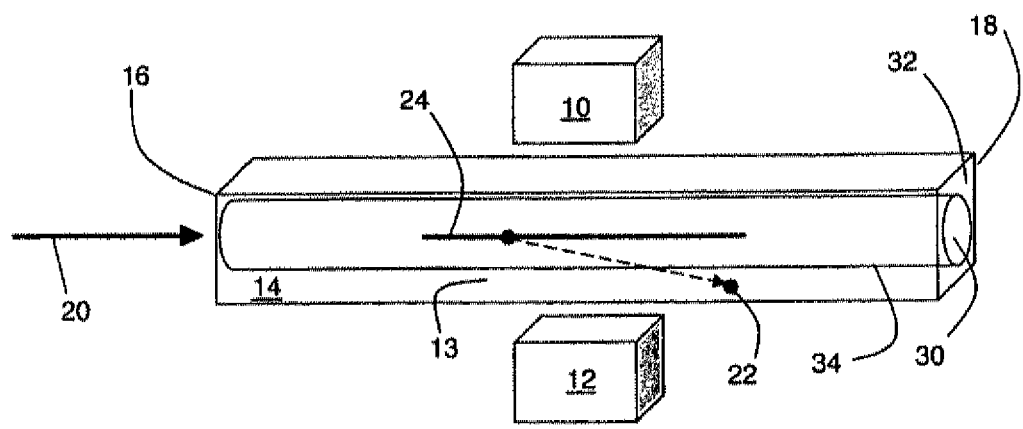
FIGS. 3A-3B include schematic illustrations of one set of embodiments in which core and cladding fluids are used.
Figure 3B:
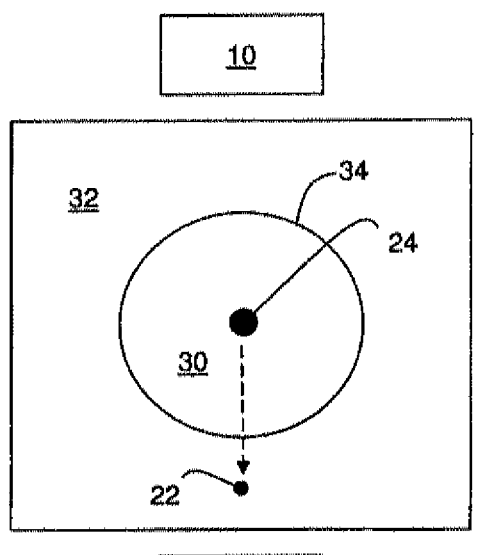

FIG. 3A includes a schematic diagram of a core/cladding flow arrangement, according to one set of embodiments, and FIG. 3B includes a cross-sectional diagram of the same arrangement. In these figures, a core fluid 30 is surrounded by cladding fluid 32, which is different from the core fluid. As non-limiting examples, in some embodiments, the core fluid is blood while the cladding fluid is saline, or the core fluid may be saline while the cladding fluid may be blood. The core fluid and the cladding fluid contact each other at an interface 34 in these figures.

In some embodiments, the core and/or the cladding fluids may contain magnetic and/or non-magnetic particles, which can be separated in some embodiments of the invention. For instance, as the core and cladding fluids pass through the magnetic field applied to the channel, one or more of the magnetic particles in either the core or cladding fluids may cross this interface due to the applied magnetic field. As an illustrative example, in FIGS. 3A-3B, magnetic particle 22 travels from the core fluid to the cladding fluid upon passing through magnetic region 13, as indicated by the dashed arrow.

Thus, in some embodiments, the magnetic field may be arranged such that one or more non-magnetic particles are transferred from the cladding fluid to the core fluid. For instance, as previously discussed, there may be magnetic particles within the channel, which may cause movement of the non-magnetic particles due to the movement of the magnetic particles under the influence of the magnetic field. Thus, in one embodiment, the non-magnetic particles may be urged to a magnetic field minimum contained within the channel, which may be a region of zero magnetic field, or otherwise define a minimum magnetic field region.

More than two fluids may also be used in some cases. For example, a core fluid, a cladding fluid, and a third fluid may be flowed through a channel. The core and cladding fluids may be flowed as described above, while the third fluid, which is different from the core fluid and the cladding fluid, surrounds the cladding fluid. The third fluid may be the same as or different from the core fluid. The magnetic fields applied to the channel may be arranged such that, as the fluids are transported through the channel, one or more magnetic or non-magnetic particles is transported from one fluid to another (e.g., from the third fluid to the core fluid, from the cladding fluid to the core fluid, from the cladding fluid to the third fluid, etc.).

Accordingly, in some embodiments, the systems and methods described herein may be used to separate one or more types of particles from one or more other types of particles, for example, magnetic particles from non-magnetic particles. Magnets may be used to produce a first portion of a fluid stream that is enriched in non-magnetic particles a second portion that is enriched in magnetic particles. The first and second enriched portions may also be separated at some point downstream of the magnetic field, as will be described in detail later.

In one set of embodiments, non-magnetic particles may be separated and/or sorted based upon differences in drag coefficients. In some embodiments, non-magnetic particles may be separated and/or sorted based upon differences in the ratio of particle volume and drag coefficient. In some embodiments, differences in drag coefficients of two particles are manifest as differences in the external surface areas of the two particles exposed to the surrounding fluid. For example, in some cases (e.g., when the non-magnetic particles are substantially spherical, etc.), particles with larger average cross-sectional diameters will have larger surface areas, and therefore, larger drag coefficients. In such cases, particles may be sorted on the basis of average diameter. As used herein, "average diameter" refers to the average of the diameters of a population of particles (e.g., non-magnetic particles). For non-spherical particles, the diameters may be approximated as the average of the distances between pairs of surface points on an object, the pairs of surface points joined by a line that intersects the center of mass of the object.

In instances where the non-magnetic particles are non-spherical, the drag coefficient may be estimated by calculating the surface area of an imaginary surface extending along the outer boundaries of the particles. As a specific example, in some embodiments, the external surface area of a porous particle may be approximated as the surface area of a theoretical sphere transcribing the particle that does not include the internal surfaces of the pores within the particle. In some embodiments, the drag coefficient of a particle may be modified by the attachment of additional entities (e.g., proteins or other polymers, etc.) to the non-magnetic particles, as discussed in more detail below.

Figure 7A:
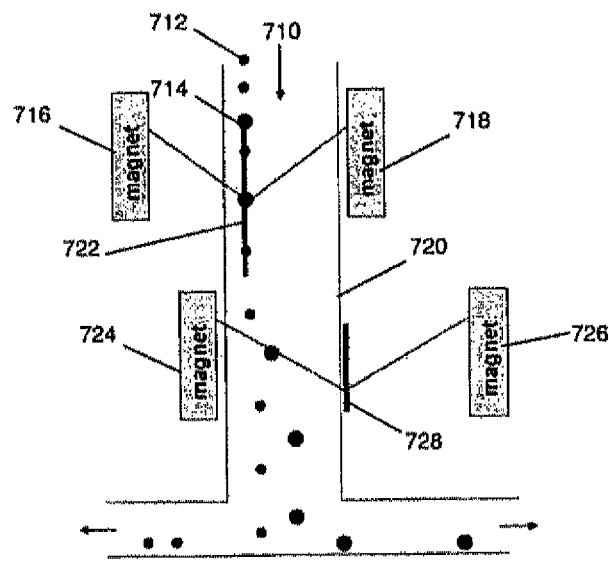
FIGS. 7A-7B include schematic diagrams of separation techniques, according to some embodiments.
Figure 7B:
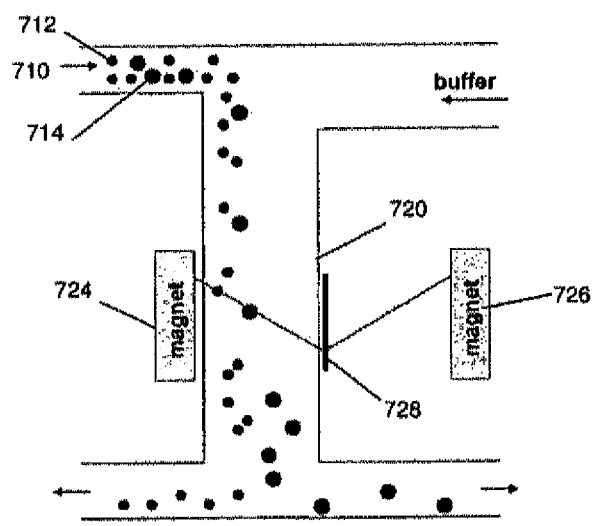

The sorting of non-magnetic particles according to differences in drag coefficients is shown in the exemplary set of embodiments illustrated in FIGS. 7A-7B. Not wishing to be bound by any theory, non-magnetic particles with relatively large drag coefficients may experience larger movement toward the magnetic field minimum than non-magnetic particles with relatively small drag coefficients in a fluid containing magnetic particles as well as the non-magnetic particles to be sorted, as the non-magnetic particles with relatively large drag coefficients may be excluded to a greater degree than the non-magnetic particles with relatively small drag coefficients. Thus, as a mixture of non-magnetic particles with larger and smaller drag coefficients are transported through a magnetic field gradient, the non-magnetic particles with larger drag coefficients may be transported across a longer distance than the non-magnetic particles with smaller drag coefficients, producing enriched streams of non-magnetic particles with larger and smaller drag coefficients, as shown in FIGS. 7A-7B. In particular, in FIG. 7A, an entering fluid 710 carrying smaller particles 712 and larger particles 714 (and also magnetic particles, as in a magnetic fluid (e.g., a ferrofluid, a solution of paramagnetic ions, etc.), not shown for purposes of clarity), is influenced by magnets 716 and 718 positioned around fluidic channel 720 so as to cause a magnetic field minimum 722 within the channel. Larger particles 714 are transported to a greater degree than the smaller particles 712 due to magnets 724 and 726 producing magnetic field minimum 728. Thus, for example in FIG. 7A, larger particles 714 can be found closer to the magnetic field minimum. It should be noted that, as shown in FIG. 7B, the magnetic field minimum need not coincide with the middle of fluidic channel 720. In addition, in some cases, there may be more than one fluid within the channel, for example, a core fluid and a cladding fluid, as previously discussed.

Thus, one set of embodiments of the present invention is directed to the separation of particles within a fluid, including the separation of magnetic particles from other magnetic particles, magnetic particles from non-magnetic particles, or non-magnetic particles from other non-magnetic particles, and such separations may be performed on the basis of drag coefficient, which may depend upon, for example other fluidic properties such as shape irregularity or cross-sectional diameter. In some cases, separations may be performed as part of a continuous sorting process. For example, in one set of embodiments, a fluid stream containing two enriched portions is passed through a T-junction, as described above in FIGS. 7A-7B.

Accordingly, in one set of embodiments, larger and smaller non-magnetic particles in a fluid containing magnetic particles may be separated using one or more magnetic fields, as noted above. Such a system can be optimized to separate particles of various diameters, depending on the application. For instance, in some embodiments, the interaction time with the magnets is chosen such that particles with relatively large diameters are transported by a certain distance while the particles with relatively small diameters are not. For example, if the channel concludes in a simple T-splitter, particles with relatively large and relatively small diameters will thus be separated into different output ports of the system. Such a system is illustrated, for example, in FIGS. 7A-7B.

In one set of embodiments, fluids enriched with particles may be separated from each other using any suitable technique, for example, using physical features within the channel. For example, referring to FIG. 1A, cylindrical baffle 50 may be positioned near outlet 18 of the channel. As the stream of magnetic and non-magnetic particles pass by the baffle, non-magnetic particles 26 may be transported through the baffle and through outlet 18B, while magnetic particles 22 may be excluded from the baffle, exiting the channel through outlet 18A. Similar types of physical separation techniques may be used, for example, to separate non-magnetic particles from other non-magnetic particles, core fluids from cladding fluids, etc. In another aspect, various devices are provided. The devices may comprise a channel around which magnets are arranged. In some cases, the magnets may be arranged such that a magnetic field minimum is produced within the channel.

Figure 4:
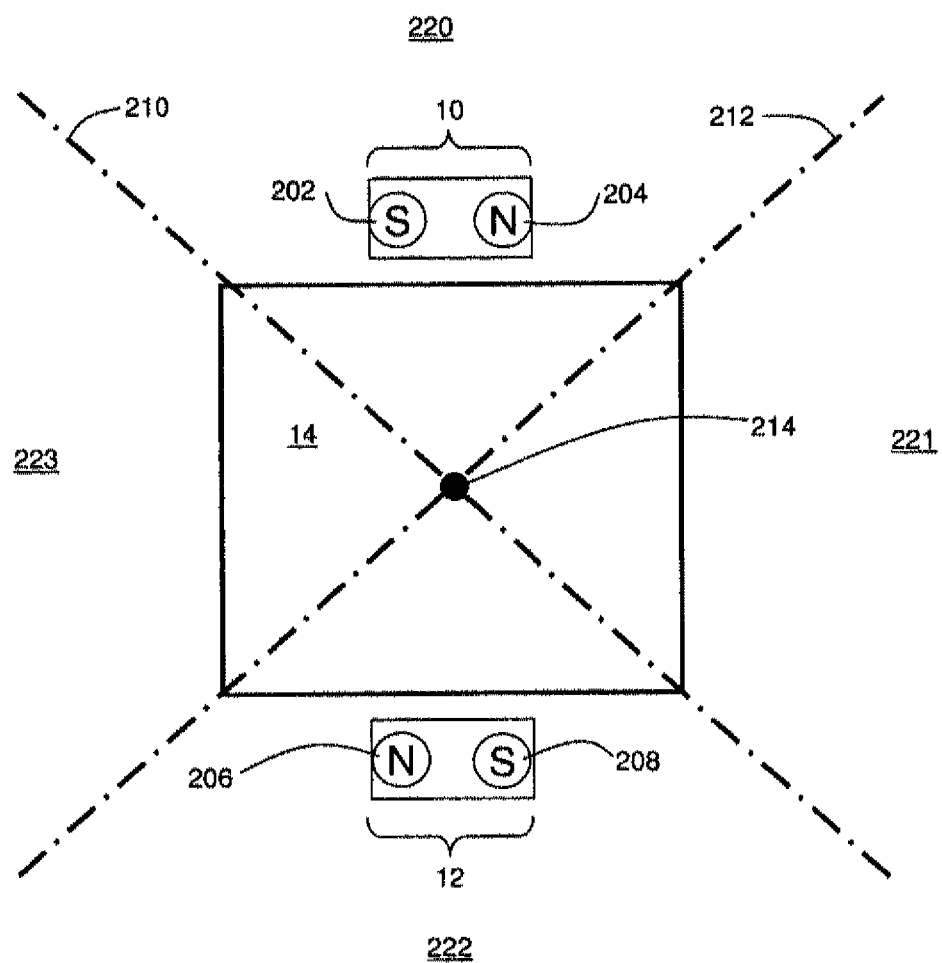
FIG. 4 includes a schematic diagram of an arrangement of magnets, according to one set of embodiments.

FIG. 4 includes a schematic diagram of another set of embodiments. In FIG. 4, two magnets, 10 and 12, are arranged around a channel such that the four magnetic poles 202, 204, 206, and 208 define a plane that is substantially perpendicular to the center axis of the microfluidic channel. In this set of embodiments, the center axis is defined by the direction of fluid flow within the microfluidic channel. FIG. 4 includes two additional axes, 210 and 212, which are drawn at 90 degrees relative to each other. Axes 210 and 212 are contained within the plane defined by the four magnetic poles and intersect at the center axis 214 of the channel. The axes are arranged to define four quadrants, 220, 221, 222, and 223. The four magnetic poles are arranged around the microfluidic channel such that two or more of the magnetic poles are contained within the same quadrant. For example, poles 202 and 204 are contained within quadrant 220, and poles 206 and 208 are contained within quadrant 222. In addition, as shown in FIG. 4, the four magnetic poles are positioned such that the distances between each magnetic pole and its nearest neighbor on either side are not substantially the same. For example, the distance between pole 206 and 208 is shorter than the distance between pole 206 and pole 202.

Figure 8:
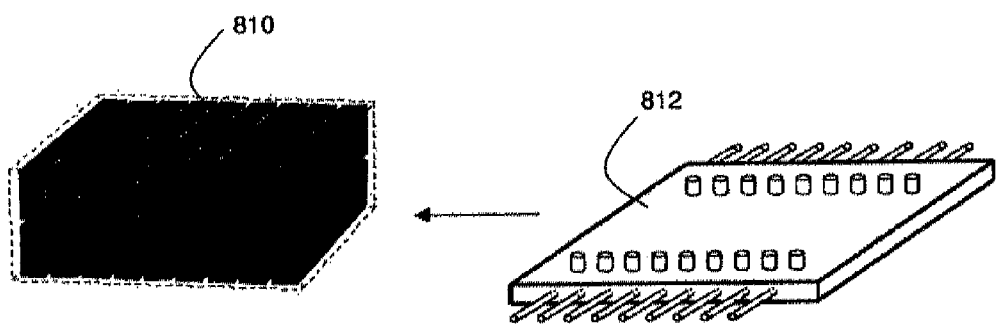
FIG. 8 includes a schematic illustration of a set of embodiments comprising multiple fluidic channels and multiple magnet pairs.

In some embodiments, the systems and method described herein may include the use of multiple channels in parallel. For example, FIG. 8 includes a schematic illustration of a multi-channel apparatus, according to one set of embodiments. The apparatus includes a series of multiple pairs of magnets 810 arranged to house a cartridge 812 comprising multiple fluidic channels. The series of magnets may be arranged such that multiple magnetic field minima are produced. When the cartridge comprising the fluidic channels is positioned within the series, for example, each channel may comprise one or more minima produced by the series of magnets. In some embodiments, the series of magnets may be reusable and the cartridge may be disposable.

In some embodiments, one or more magnetic fields applied to the fluid may have a relatively large magnetic field gradient. Relatively large magnetic field gradients may be useful in achieving fast transport of magnetic and/or non-magnetic particles. Larger magnetic field gradients may also lead to more complete separation of magnetic and non-magnetic particles than would occur with relatively small gradients. For example, the use of relatively larger magnetic field gradients allows one to perform a separation of non-magnetic and magnetic particles over a relatively short channel distance, compared to the distance of the channel that would be required were the magnetic field gradient smaller. In addition, larger magnetic field gradients may enable improved particle separation. In some instances, the magnetic field may have a gradient of at least about 0.1 T/mm, at least about 0.5 T/mm, at least about 1 T/mm, at least about 5 T/mm, at least about 10 T/mm, or greater along a dimension substantially perpendicular to the flow of fluid within the channel. The magnetic field gradients disclosed herein can be calculated using the surface fields of the permanent magnets as provided by the manufacturer. Magnetic fields and gradients can be experimentally measured using a Gaussmeter including a Hall probe, according to techniques known to those skilled in the art.

In some instances, the magnetic field may be arranged such that a magnetic field minimum is positioned along any line or at any point within the channel. For example, in some embodiments, the magnetic field may be arranged such that a magnetic field minimum (e.g., a magnetic field zero) is positioned closer to one wall of the channel relative to the other walls, or the magnetic filed minimum may be positioned in the center of the channel. In some cases, the magnetic field minimum may be positioned near a corner of a square channel. In some embodiments, the system includes one or more magnetic field minima outside the channel. In addition, some embodiments include multiple magnetic field minima arranged inside a single channel.

In some embodiments, a first magnetic field is applied to a first portion of a channel and a second magnetic field is applied to a second portion of the channel. The second magnetic field has, in some cases, a magnetic field distribution that is different from that of the first magnetic field. For example, the first magnetic field may comprise a first magnetic field minimum (e.g., parallel to the direction of fluid flow) located at a first distance from the center axis of the channel, while the second magnetic field comprises a second magnetic field minimum (e.g., parallel to the direction of fluid flow) located a second distance from the center axis of the channel. Such arrangements may be used, for example, to separate particles (e.g., magnetic and/or non-magnetic particles) on the basis of diameter (e.g., as shown in FIGS. 2A-2B), charge, or other property that affects its transport through a magnetic field.

Figure 2A:
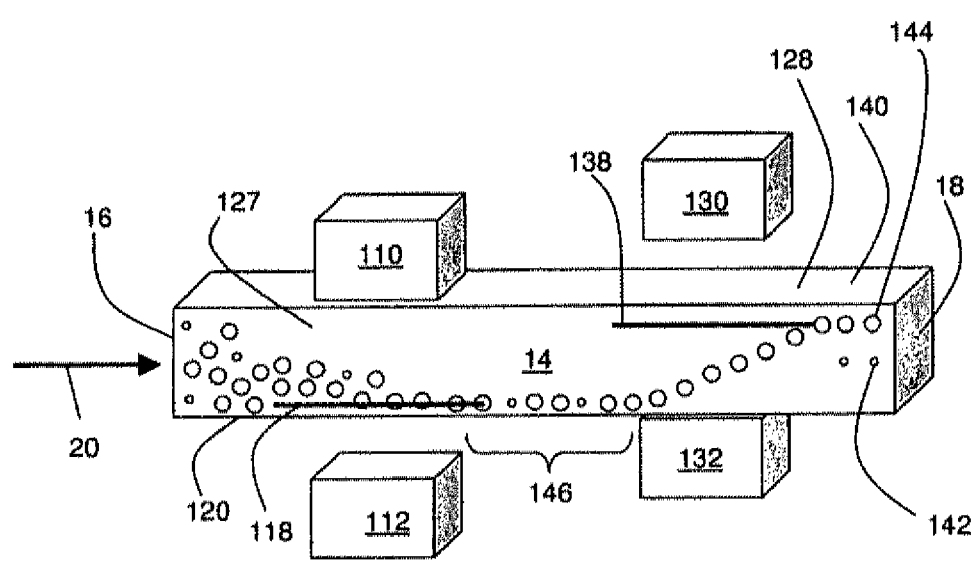
FIGS. 2A-2B illustrate another set of embodiments, wherein a device includes two magnetic fields.
Figure 2B:
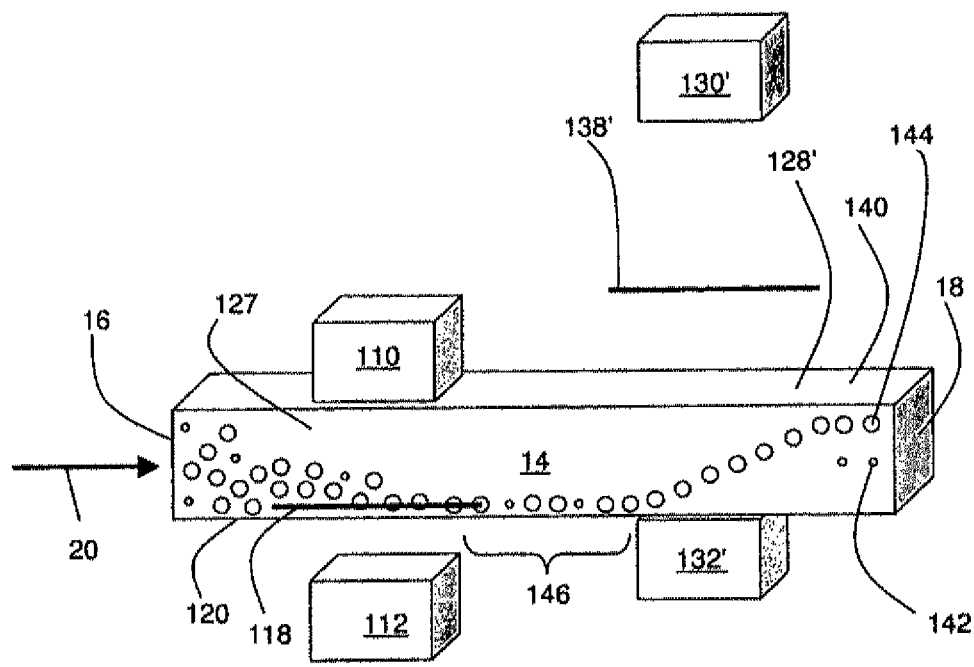

For example, in one set of embodiments illustrated in FIG. 2A, a first magnetic field is arranged between magnets 110 and 112 such that a magnetic field minimum 118 is positioned relatively close to wall 120 of channel 14. A second magnetic field may be arranged between magnets 130 and 132 such that a second magnetic field minimum 138 is positioned relatively close to opposing wall 140 of channel 14. As a fluid comprising magnetic and non-magnetic particles is passed through the channel from the first magnetic field region 127 to the second magnetic field region 128, individual non-magnetic particles may be deflected different distances. For example, smaller non-magnetic particles (e.g., 142 in FIGS. 2A-2B) may be deflected shorter distances than larger non-magnetic particles (e.g., 144 in FIGS. 2A-2B). In some embodiments, particles with multiple charges may be deflected longer distances than particles with single charges or no charge.

In some embodiments, the first and second magnetic field minima are located within the channel. In other embodiments, at least one of the first and second magnetic field minima are located outside the channel. For example, in FIG. 2B, magnets 130' and 132' are arranged such that the resultant magnetic field minimum 138' lies outside the volume of channel 14. In some embodiments, positioning the magnets in such a way may increase the magnetic field gradient within the portion of the channel through which the magnetic field passes (e.g., second magnetic field region 128' in FIG. 2B). This may lead, for example, to an increase in the distance over which objects (e.g., magnetic and/or non-magnetic particles) are displaced within the channel.

In some embodiments, more than two magnetic fields may be employed, producing more than two magnetic field minima. In some embodiments, all of the minima may lie within the fluidic channel, while in other embodiments, one or more minima may be positioned outside the fluidic channel.

In some aspects, magnetic fields may be used as described above to achieve a predetermined distribution of particles within the channel. In some cases, particles may be arranged within a narrow band, as measured radially within the channel. For example, in some cases, after passing the fluid through the magnetic field, at least about 90% of the non-magnetic particles are transported to a region comprising no more than about 50%, about 30%, about 10%, about 5%, or about 2% of a cross-sectional dimension of the channel. As used herein, a "cross-sectional dimension" is measured perpendicular to fluid flow. In some embodiments, at least about 95%, at least about 98%, at least about 99%, or at least about 99.9% of the non-magnetic particles are transported to a region comprising no more than about 50%, about 30%, about 10%, about 5%, or about 2% of a cross-sectional dimension of the channel. In some cases, the about 50%, about 30%, about 10%, about 5%, or about 2% of the cross-sectional dimension of the channel may contain the center axis, while in other embodiments, the about 50%, about 30%, about 10%, about 5%, or about 2% of the cross-sectional dimension may lie in other regions of the channel not containing the center axis.

In some embodiments, after passing the fluid comprising magnetic and non-magnetic particles through the magnetic field, the non-magnetic particles may be arranged such that no line drawn from a first wall of the channel, normal to the first wall, to a second wall of the channel intersects more than one non-magnetic particle (i.e., in a "single-file" arrangement). A single-file row of non-magnetic particles within a channel is illustrated in region 146 of FIGS. 2A-2B. Such a single-file arrangement of particles may be useful in separating particles. For example, in some embodiments, optical sorting based on refractive index differences between cells may be performed. As a specific example, cells containing large amounts of protein may have a higher average refractive index than those containing little protein, and will therefore travel a longer distance upon interaction with light (e.g., a laser).

In some embodiments, one or more labeling steps may be performed to achieve separation of two or more types of non-magnetic particles. In some embodiments, the step of tagging two or more types of non-magnetic particles may be used to establish differences in the drag coefficients of two or more types of non-magnetic particles. For example, in one set of embodiments, a first tag (e.g., a first, relatively short polymer chain) may be selectively attached to a first type of non-magnetic particle. A second tag (e.g., a second, relatively long polymer chain) may be selectively attached to a second type of non-magnetic particle. The first and second types of non-magnetic particles may then be separated from each other based on differences in their drag coefficients (e.g., due to differences in their external surface areas, or some other property). In some embodiments, two, three, four, or more types of non-magnetic particles may be separated using a similar method. For example, gold nano-particle-labels could be used to increase the optical interaction strength of specific target objects. In another set of applications, antibody binding may be used. Despite the fact that antibodies bind strongly to one specific corresponding binding partner, complex samples, in some cases, include a variety of different cells that express surface proteins specific to the tagged antibody. In such cases, multi-parameter tagging may be used to remove these ambiguities and achieve high enrichment factors for the target cells. In one set of embodiments, polymer tags (e.g. DNA) of different lengths that alter the drag coefficient of the object they have been attached to may be used. If the objects to be sorted (e.g., cells) are of similar size (e.g., similar diameter) but have different drag coefficients (e.g., determined by the polymer tags), their relative displacements in a magnetic fluid may be determined by the size of the tags. Such a passive sorting scheme would not involve, in some embodiments, optical analysis, feedback, or active switching.

In some cases, non-magnetic particles may be focused prior to being transported through a magnetic field and separated (e.g., separated from magnetic particles, separated based upon size, etc.). For example, in some embodiments, a magnetic field may be used to arrange non-magnetic particles within a narrow band, as measured radially within the channel, as described above. The narrow band of non-magnetic particles may then be passed through a magnetic field, and the non-magnetic particles may be sorted (e.g., according to differences in size, drag coefficient, or any other basis described herein). In some cases, hydrodynamic focusing may be used to produce a focused stream of non-magnetic particles. Examples of systems and methods for the production of hydrodynamically focused streams of non-magnetic particles are described, for example, in International Patent Application Serial No. PCT/US2004/010903, filed Apr. 9, 2004, published as WO2004/091763 on Oct. 28, 2004, entitled "Formation and Control of Fluidic Species," to Link et al.; International Patent Application Serial No. PCT/US03/20542, filed Jun. 30, 2003, published as WO 2004/002627, entitled "Method and Apparatus for Fluid Dispersion," to Stone et al.; International Patent Application Serial No. PCT/US2006/007772, filed Mar. 3, 2006, published as WO 2006/096571, entitled "Method and Apparatus for Forming Multiple Emulsions," to Weitz et al.; and International Patent Application Serial No. PCT/US2004/027912, filed Aug. 27, 2004, published as WO2005/021151 on Mar. 10, 2005, entitled "Electronic Control of Fluidic Species," to Link et al.; all of which are incorporated herein by reference in their entireties.

A variety of materials and methods, according to certain aspects of the invention, can be used to form systems (such as those described above) able to manipulate magnetic and non-magnetic particles. For example, various components can be formed from solid materials, in which the channels can be formed via micromachining, film deposition processes such as spin coating and chemical vapor deposition, laser fabrication, photolithographic techniques, etching methods including wet chemical or plasma processes, and the like. See, for example, Scientific American, 248:44-55, 1983 (Angell, et al). In one embodiment, at least a portion of the fluidic system is formed of silicon by etching features in a silicon chip. Technologies for precise and efficient fabrication of various fluidic systems and devices of the invention from silicon are known. In another embodiment, various components of the systems and devices of the invention can be formed of a polymer, for example, an elastomeric polymer such as polydimethylsiloxane ("PDMS"), polytetrafluoroethylene ("PTFE" or Teflon®), or the like.

Different components can be fabricated of different materials. For example, a base portion including a bottom wall and side walls can be fabricated from an opaque material such as silicon or PDMS, and a top portion can be fabricated from a transparent or at least partially transparent material, such as glass or a transparent polymer, for observation and/or control of the fluidic process. Components can be coated so as to expose a desired chemical functionality to fluids that contact interior channel walls, where the base supporting material does not have a precise, desired functionality. For example, components can be fabricated as illustrated, with interior channel walls coated with another material. Material used to fabricate various components of the systems and devices of the invention, e.g., materials used to coat interior walls of fluid channels, may desirably be selected from among those materials that will not adversely affect or be affected by fluid flowing through the fluidic system, e.g., material(s) that is chemically inert in the presence of fluids to be used within the device.

In one embodiment, various components of the invention are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, or mixture of such polymers heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

Silicone polymers are preferred in one set of embodiments, for example, the silicone elastomer polydimethylsiloxane.

Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying fabrication of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric, and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, components can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," Anal. Chem., 70:474-480, 1998 (Duffy, et al.), incorporated herein by reference.

In some embodiments, certain microfluidic structures of the invention (or interior, fluid-contacting surfaces) may be formed from certain oxidized silicone polymers. Such surfaces may be more hydrophilic than the surface of an elastomeric polymer. Such hydrophilic channel surfaces can thus be more easily filled and wetted with aqueous solutions.

In one embodiment, a bottom wall of a microfluidic device of the invention is formed of a material different from one or more side walls or a top wall, or other components. For example, the interior surface of a bottom wall can comprise the surface of a silicon wafer or microchip, or other substrate. Other components can, as described above, be sealed to such alternative substrates. Where it is desired to seal a component comprising a silicone polymer (e.g. PDMS) to a substrate (bottom wall) of different material, the substrate may be selected from the group of materials to which oxidized silicone polymer is able to irreversibly seal (e.g., glass, silicon, silicon oxide, quartz, silicon nitride, polyethylene, polystyrene, epoxy polymers, and glassy carbon surfaces which have been oxidized). Alternatively, other sealing techniques can be used, as would be apparent to those of ordinary skill in the art, including, but not limited to, the use of separate adhesives, bonding, solvent bonding, ultrasonic welding, etc.

U.S. Provisional Patent Application Ser. No. 61/168,519, filed Apr. 10, 2009, entitled "Manipulation of Particles in Channels," by Stone, et al. is incorporated herein by reference in its entirety.

The following examples are intended to illustrate certain embodiments of the present invention, but are not to be construed as limiting and do not exemplify the full scope of the invention.

EXAMPLE 1

In this example, magnets were arranged around a channel to produce a magnetic field including a region having zero magnetic field intensity within the channel. Such arrangements may be used to separate non-magnetic particles from solutions of magnetic particles, as is discussed herein.

Figure 9:
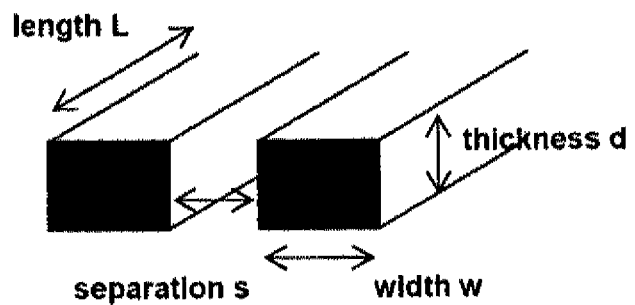
FIG. 9 includes, according to one set of embodiments, a schematic illustration of a magnet arrangement.

Two rectangular permanent magnets (length L, width w, thickness d) were arranged in parallel such that the magnetization vectors of the two magnets pointed in opposite directions without facing each other directly (see FIG. 9). This arrangement created a region having zero magnetic field intensity on the line of symmetry between the two magnets.

Figure 10:
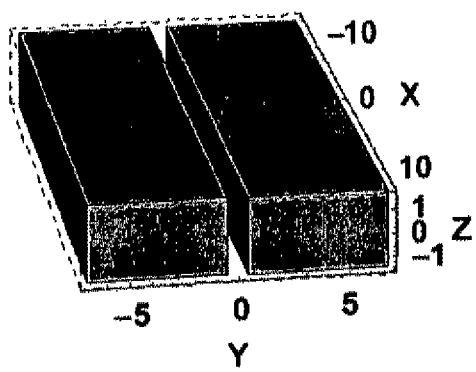
FIG. 10 includes a schematic illustration of a magnet arrangement, according to one set of embodiments.
Figure 11A:
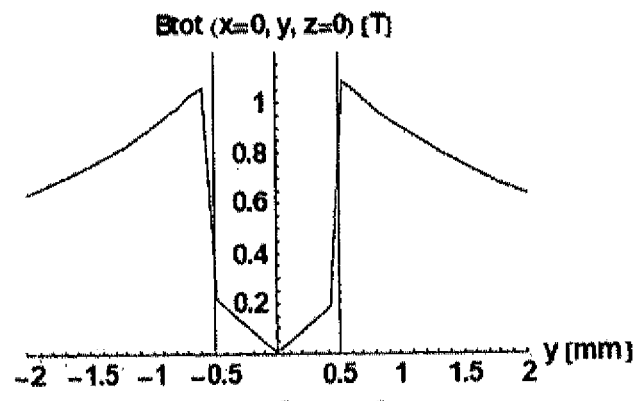
FIGS. 11A-11C include plots of the magnetic field as a function of position, according to one set of embodiments.
Figure 11B:
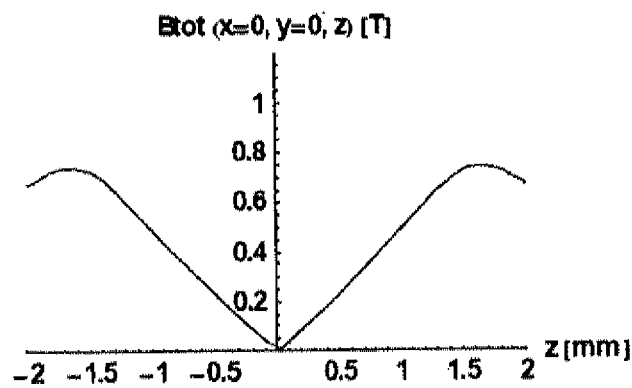
Figure 11C:
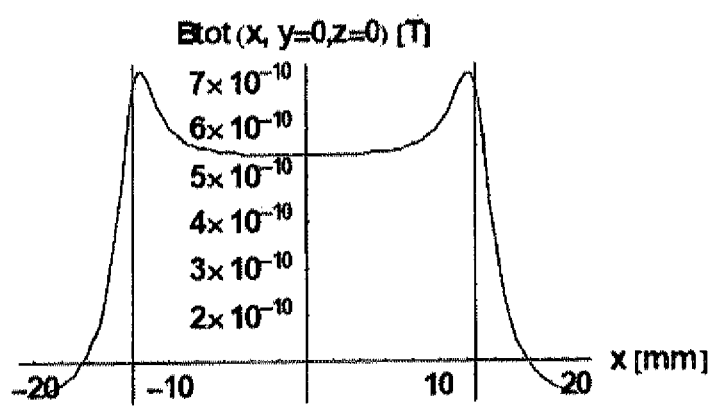
Figure 12A:
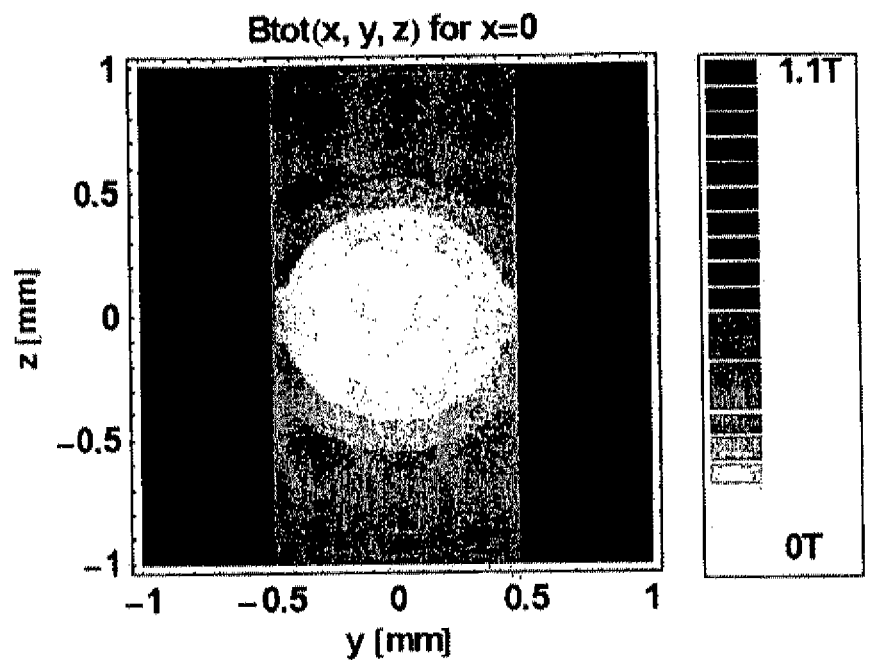
FIGS. 12A-12C include, according to one set of embodiments, contour plots of the magnitude of the magnetic field as a function of position.
Figure 12B:
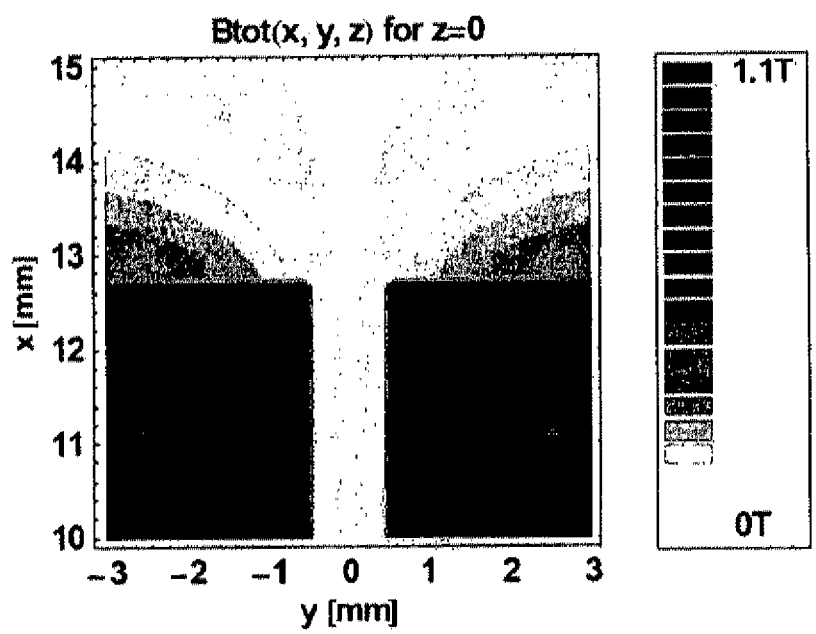
Figure 12C:
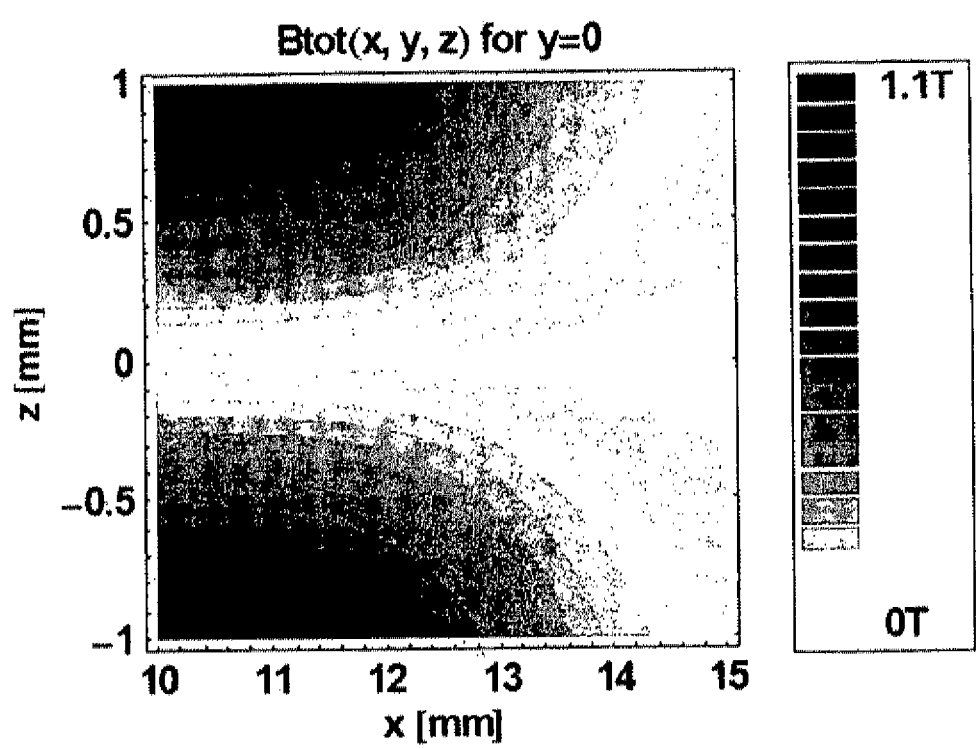

Simulated magnetic field diagrams were produced using Mathematica. FIGS. 11A-11C show plots of the total magnetic field $B_{tot}$ [x, y, z] for the following cases: $B_{tot}$[0,0,z] vs. z, $B_{tot}$[0,y,0] vs. y, and $B_{tot}$[x,0,0] vs. x. FIGS. 12A-12C show contour plots of the magnetic potential for the following cases: $B_{tot}$[0,y,z] in the yz-plane, $B_{tot}$[x,y,0] in the xy-plane, and $B_{tot}$[x,0,z] in the xz-plane. In these figures, the magnets are located at positions (0,−s/2,0) and (0,s/2,0), where s is the separation between the magnets. In these simulations, L=25.4 mm, w=3.2 mm, d=1.6 mm and s=1 mm (see FIG. 10).

The plots showed that the magnetic fields varied in the longitudinal direction by relatively small negligible amounts (e.g., on the order of $10^{-10}$ T/mm). In contrast, transverse gradients were achieved that scaled roughly as the surface field intensity of the permanent magnets divided by s/2, where s was the separation between the magnets. For instance, for typical NdFeB permanent magnets and a 1-mm separation between the magnets, magnetic field gradients on the order of 0.5 T/mm could be achieved.

EXAMPLE 2

In this example, an example illustrating manipulating non-magnetic particles within a solution of paramagnetic ions is described. In this example, polystyrene beads with diameters of 10 to 15 microns were used as non-magnetic particles. The beads were mixed with a 200 mM solution of Gd-DTPA (diethylene triamine pentaacetic acid), to a concentration of 0.0001% solid components by weight. The solution was transported at volumetric flow rates of 1-2 microliters per minute. The magnets were aligned with the centers of the sidewalls of the capillary tube.

Figure 13A:
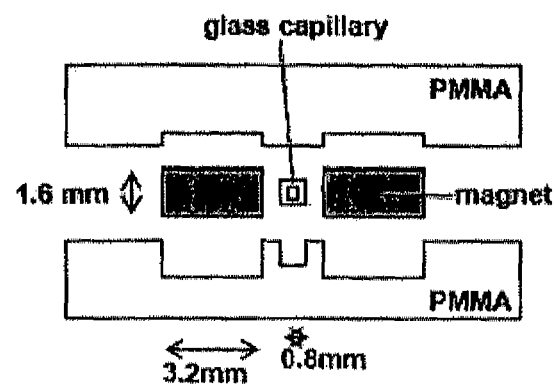
FIGS. 13A-13B include schematic diagrams of an experimental setup, according to one set of embodiments.

FIG. 13A incudes a cross-sectional schematic illustration of the experimental setup used in this example. The magnets and capillary were mounted into a PMMA (poly(methyl methacrylate)) structure in order to produce an overlapping magnetic field with a magnetic field zero at the center plane of the channel. The permanent magnets had dimensions of 1.6 mm×3.2 mm×25 mm and surface fields of 0.4 T. The square glass capillary had inner (outer) dimensions of 400 microns (800 microns) and a length of 10 cm. The length of the PMMA structure was 7.5 cm. A top view of the experimental setup is shown in FIG. 13B.

Figure 13B:
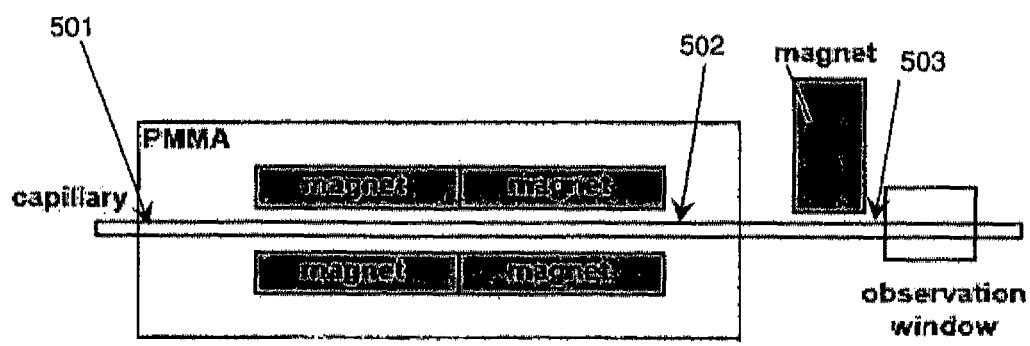
Figure 14A:
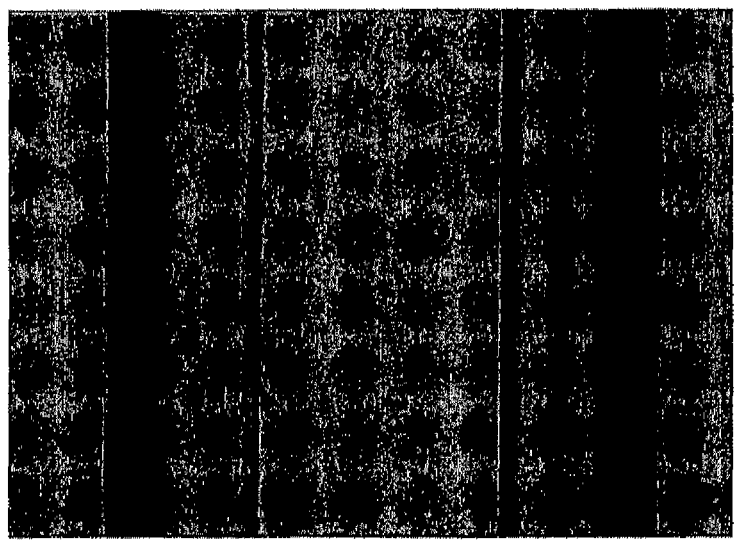
FIGS. 14A-14C include micrographs of fluidic channels containing non-magnetic particles, according to one set of embodiments.
Figure 14B:
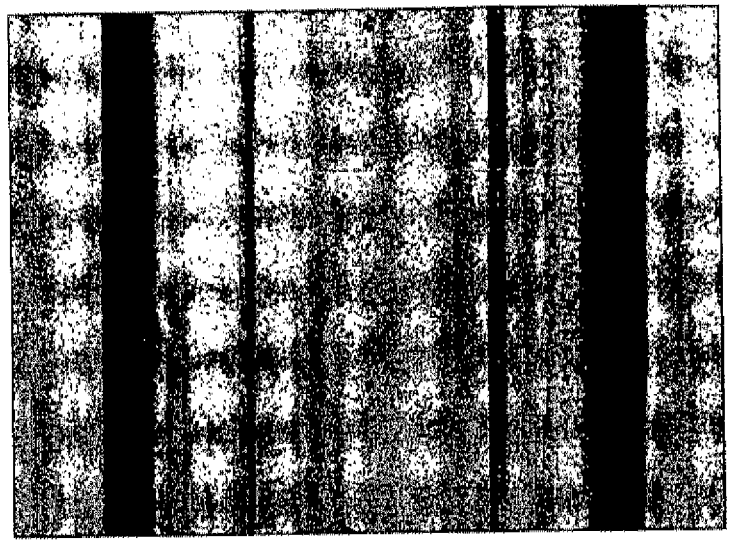
Figure 14C:
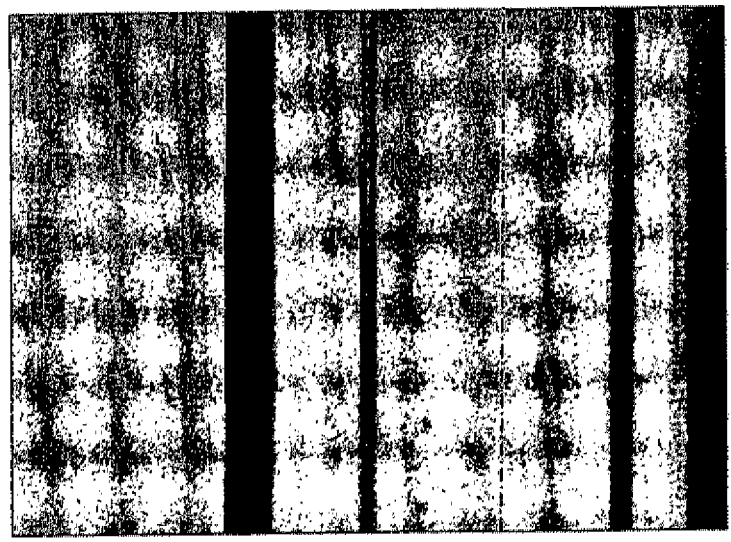

FIG. 14A includes a micrograph of non-magnetic particles (with diameters of 10 and 15 microns) before reaching the focusing magnets (region 501 in FIG. 13B). Non-magnetic particles suspended in magnetic fluid were focused to single file movement at the center of the channel by aligning the center of the capillary with the magnetic field zero created by the permanent magnets. An optical micrograph of focused non-magnetic particles (at region 502 in FIG. 13B) is shown in FIG. 14B. After focusing was achieved, the particles were sorted according to diameter using an additional magnet located downstream of the focusing magnets. FIG. 14C shows an optical micrograph of sorted non-magnetic particles (e.g., at region 503 in FIG. 13B). Note that the larger non-magnetic particles have been transported a longer distance from the center axis of the channel (indicated by the dashed line).

EXAMPLE 3

In this example, the movement of non-magnetic particles is theoretically described, although it should be understood that this theory is presented by way of illustration only, and is not intended to be limiting in any way. In this example, the movement of magnetic particles away from the magnetic field minimum (toward regions comprising high magnetic fields) may force the non-magnetic particles toward the magnetic field minimum. This effect may be used, for example, to produce relatively concentrated populations of magnetic and non-magnetic particles, as described above.

The force on a non-magnetic particle in a solution of paramagnetic ions may be expressed as:

$$F_m = \frac{(\chi_f - \chi_o)}{\mu_0} C \cdot V \cdot (B \cdot \nabla)B \quad [1]$$

where $(\chi)_o$ represents the susceptibility of the particles, $(\chi)_f$ is the susceptibility of the paramagnetic ions, $(\mu)_o$ is the permeability of vacuum, C is the concentration of the paramagnetic ions, V is the volume of the particle, and B is the magnetic field. This equation holds under the assumption that the magnetic energy of the volume displaced by the object is larger than $k_B T$ where $k_B$ is the Boltzmann-constant and T is the temperature. The drag force on a spherical object of radius R is given by $$F_{drag} = 6\pi \eta R v$$

where eta is the viscosity of the fluid and v is the velocity of the object. The terminal velocity of an object that is exposed to magnetic fluid forces is calculated as:

$$v_t = \frac{(\chi_f - \chi_o) \cdot C \cdot V}{\beta \cdot \mu_0}(B \cdot \nabla)B \quad [3]$$

where beta is the drag coefficient of the object.

As non-magnetic particles pass through the magnetic field, the forces described above act to transport the non-magnetic particles toward the magnetic field zero. After passing the non-magnetic particles through the magnetic field, the particles may be focused into a relatively narrow region of the channel, as shown in FIG. 2.

Figure 5A:
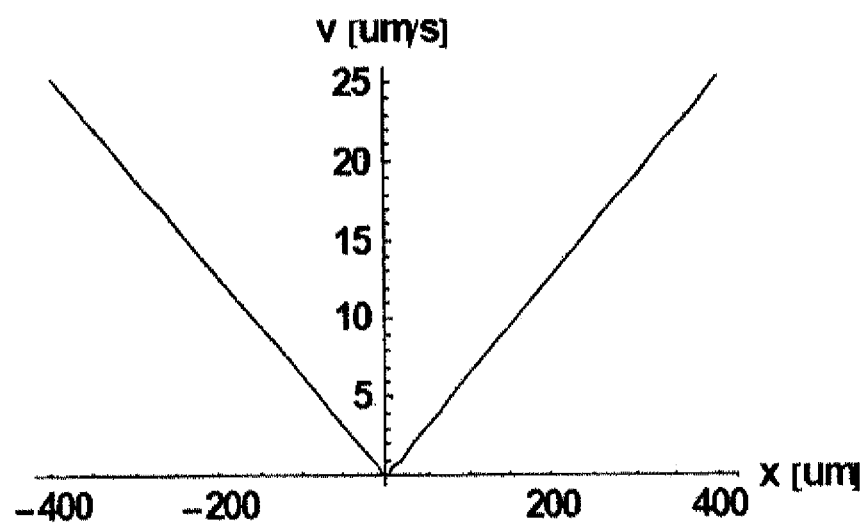
FIGS. 5A-5B include plots of terminal velocity as a function of distance from a magnetic field minimum center and the corresponding displacement as a function of time, according to one set of embodiments.
Figure 5B:
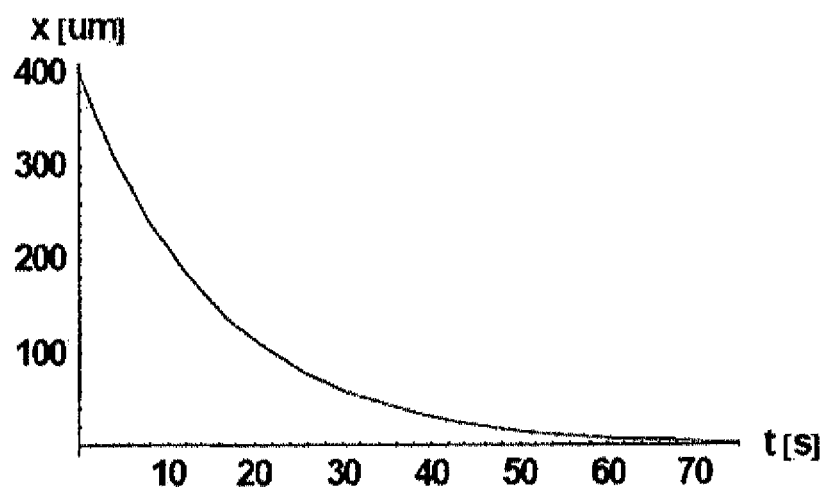

In some embodiments, the force exerted on objects by the magnetic field decreases as the objects approach a magnetic field minimum due to the dependence of the force on the absolute value of the magnetic field. FIG. 5A shows a plot of the terminal velocity of a polystyrene bead with radius R=10 microns in a gadolinium-ion solution (200 mM) exposed to a linear magnetic field gradient of 0.8 T/mm as a function of distance from the magnetic field minimum center, and FIG. 5B shows the corresponding displacement as a function of time, assuming the bead starts out at a distance of 400 microns away from the position of the magnetic field minimum. Due to the quadratic dependence of the force on the size of the object, this effect is more prominent for smaller objects.

EXAMPLE 4

This prophetic example describes embodiments in which more than one pair of magnets are used to manipulate non-magnetic particles. This technique may be especially useful when employing magnetic field gradients with a non-zero second derivative. Vanishing forces at the magnetic field minimum can be avoided by altering the transverse position of the magnetic field minimum in order to prevent objects from approaching the region where the forces vanish.

Figure 6:
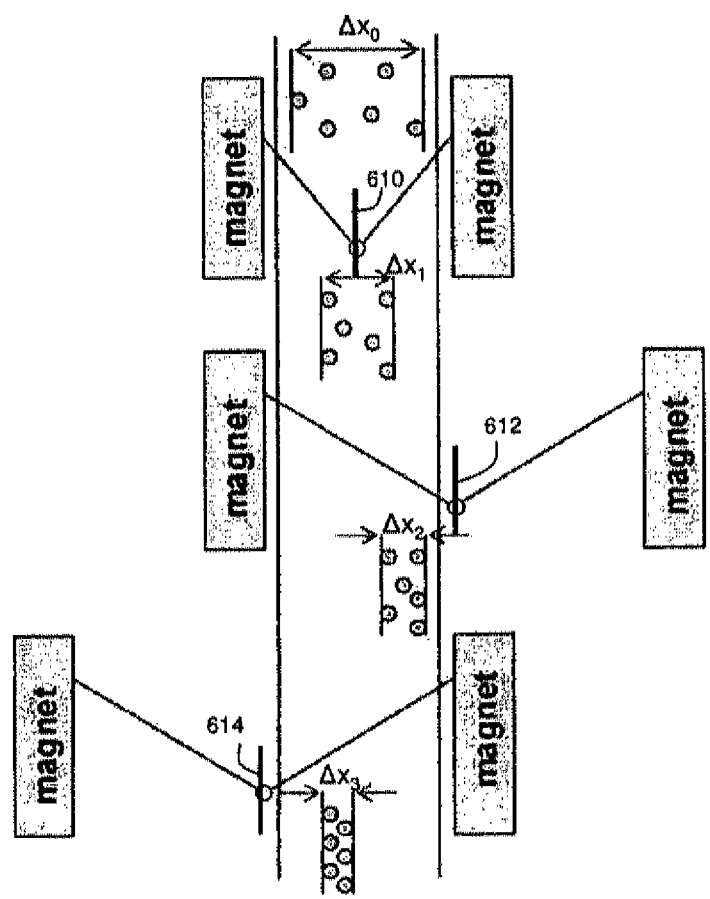
FIG. 6 includes, according to one set of embodiments, a schematic illustration of a device including multiple magnetic fields.

FIG. 6 includes a schematic diagram outlining one such embodiment. In this set of embodiments, a stream of particles (e.g., non-magnetic particles) that is distributed over the width of the channel is passed through a first magnetic field that is arranged such that the magnetic field minimum coincides substantially with the center of the channel, as indicated by region 610 in FIG. 6. The interaction time with the magnetic field generated by the first set of magnets (given by the ratio of $L/v_{flow}$ where L is the length of the magnet and $v_{flow}$ is the average flow velocity) can be chosen such that the transverse terminal velocity does not fall below the minimal value $v_{t,min}$. The distribution of non-magnetic particles is compressed from $\Delta x_0$ to $\Delta x_1$ by the first set of magnets.

In this example, the second set of magnets is arranged such that the magnetic field zero lies outside the channel, as indicated by region 612. The incoming distribution of non-magnetic particles interacts with the field on only one side of the magnetic field zero. Thus all of the beads experience a force in the same direction.

However, since the force also depends on the absolute value of the magnetic field, those particles closer to the magnetic field minimum will experience less of a force than those further away from the magnetic field minimum. This leads to a compression of the particle distribution to $\Delta x_2$. Because there will still be a net movement toward the magnetic field minimum, it may be advantageous to choose the interaction time such that the terminal velocity of the particles furthest away from the trap center does not fall beyond the previously defined value $v_{min}$.

In this example, the third set of magnets is arranged such that the magnetic field minimum, as indicated by region 614, lies outside the channel, but on the side opposite the magnetic field minimum established by the second set of magnets. Thus, the distribution of particles enters the interaction region with the magnets at a transverse position relatively far away from the trap center, thus leading to relatively high terminal velocities and further compression. In some cases, the interaction can be selected so as to achieve the maximum amount of compression without using magnets with unreasonably long dimensions. This process may be repeated any number of times to achieve the desired separation.

EXAMPLE 5

This example presents theoretical calculations that describe certain embodiments in which magnetic forces are used to separate magnetic or non-magnetic particles on the basis of diameter. However, this example is presented here by way of illustration only, and is not intended to be limiting.

Referring to Equation 3, the terminal velocity may be calculated as:

$$v_t = \frac{(\chi_f - \chi_o) \cdot C \cdot V}{\beta \cdot \mu_0}(B \cdot \nabla)B \quad [3]$$

The drag coefficient is dependent upon the diameter, shape, and surface properties of the object, as well as the viscosity of the fluid. At the end of the interaction time t during which the force F is applied, the object is displaced by a distance of:

$$x(t) = v_t \cdot t \quad [4]$$

If a distribution of identical objects is centered around $x(t=0)=0$ with a spread of $\Delta x_i$, after time t, the distribution will be centered around $x(t)=vt \cdot t$ with the same spread of $\Delta x_i$.

If the objects are not identical, but rather vary with respect to the average drag coefficient beta by $\Delta$beta, the spatial spread among the objects may be calculated by:

$$\Delta x_{drag} = F \cdot (\Delta \text{beta})/[(\text{beta})^2 - (\Delta \text{beta})^2] \cdot t \quad [5]$$

Finally, if the force F varies by $\Delta F$ (e.g., as a result of varying properties among the non-identical objects such as a variation in the number of magnetic tags), the spatial spread may be calculated as:

$$\Delta x_F = \Delta F/(\text{beta}) \cdot t \quad [6]$$

The total width of the final spatial distribution centered around x(t) would thus be calculated as:

$$\Delta x_{tot} = \Delta x_i + \Delta x_{drag} + \Delta x_F = \Delta x_i + \{F \cdot (\Delta \text{beta})/[(\text{beta})^2 - (\Delta \text{beta})^2] + \Delta F/(\text{beta})\} \cdot t \quad [7]$$

If the total displacement $(x(t)=vt \cdot t)$ of the center of the distribution is larger than $\Delta x_{tot}/2$, all objects of interest can be isolated from the rest of the sample.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:
applying a magnetic field to a channel containing a core fluid and a cladding fluid surrounding the core fluid, the cladding fluid being different from the core fluid and contacting the core fluid at an interface, at least one of the core and cladding fluids containing magnetic particles, wherein at least some of the magnetic particles cross the interface due to the applied magnetic field.

2. The method of claim 1, further comprising flowing the core and cladding fluids through the channel.

3. The method of claim 1, wherein the channel is a microchannel.

4. The method of claim 1, further comprising separating the core fluid from the cladding fluid.

5. The method of claim 4, further comprising separating the core fluid from the cladding fluid downstream of the magnetic field.

6. The method of claim 1, wherein the magnetic field is generated by a permanent magnet.

7. The method of claim 1, wherein the magnetic field is generated by an electromagnet.

8. The method of claim 1, wherein the magnetic field is arranged such that a magnetic field minimum is positioned substantially along a center axis of the channel, the center axis being defined in a direction of fluid flow within the channel.

9. The method of claim 1, wherein the magnetic field is applied to a first portion of the channel, the method further comprising applying a second magnetic field to a second portion of the channel different from the first portion of the channel.

10. The method of claim 9, wherein the second magnetic field has a magnetic field distribution that is different from that of the first magnetic field.

11. The method of claim 1, wherein at least some of the magnetic particles are fastened to cells.

12. The method of claim 1, wherein the core fluid and/or cladding fluid comprises saline.

13. The method of claim 1, wherein the core fluid and/or cladding fluid comprises blood.

14. The method of claim 1, wherein the core fluid comprises blood and the cladding fluid comprises saline.

15. The method of claim 1, further comprising providing a third fluid surrounding the cladding fluid, the third fluid being different from the cladding fluid and contacting the cladding fluid at a second interface.

16. The method of claim 15, further comprising separating the core fluid, the cladding fluid, and the third fluid.

17. The method of claim 1, wherein at least some of the magnetic particles are transported from the core fluid to the cladding fluid due to the applied magnetic field.

18. The method of claim 1, wherein at least some of the magnetic particles are transported from the cladding fluid to the core fluid due to the applied magnetic field.

19. The method of claim 1, wherein at least one of the core and cladding fluids contains non-magnetic particles.

20. The method of claim 19, wherein the cladding fluid contains non-magnetic particles.

21. The method of claim 20, wherein at least some of the non-magnetic particles are transported from the cladding fluid to the core fluid due to the applied magnetic field.

22. The method of claim 1, wherein the core fluid and the cladding fluid are immiscible.

* * * * *